US010183173B2

(12) United States Patent
Imamura

(10) Patent No.: US 10,183,173 B2
(45) Date of Patent: Jan. 22, 2019

(54) CONTENT OUTPUT DEVICE, CONTENT OUTPUT METHOD, CONTROL DEVICE, AND CONTROL METHOD

(71) Applicant: Sony Corporation, Tokyo (JP)

(72) Inventor: Shoji Imamura, Tokyo (JP)

(73) Assignee: SONY CORPORATION, Tokyo (JP)

(*) Notice: Subject to any disclaimer, the term of this patent is extended or adjusted under 35 U.S.C. 154(b) by 599 days.

(21) Appl. No.: 14/405,039

(22) PCT Filed: Apr. 30, 2013

(86) PCT No.: PCT/JP2013/062623
§ 371 (c)(1),
(2) Date: Dec. 2, 2014

(87) PCT Pub. No.: WO2014/020960
PCT Pub. Date: Feb. 6, 2014

(65) Prior Publication Data
US 2015/0148586 A1 May 28, 2015

(30) Foreign Application Priority Data
Jul. 31, 2012 (JP) .................. 2012-169564

(51) Int. Cl.
*A61N 1/00* (2006.01)
*A61N 2/02* (2006.01)
*H04R 5/033* (2006.01)
*A61M 21/00* (2006.01)
*A61N 2/00* (2006.01)

(52) U.S. Cl.
CPC ............... *A61N 2/02* (2013.01); *A61M 21/00* (2013.01); *A61N 2/002* (2013.01); *A61N 2/006* (2013.01); *H04R 5/0335* (2013.01); *A61M 2021/0027* (2013.01); *A61M 2021/0055* (2013.01)

(58) Field of Classification Search
CPC ..................... A61M 2021/0055; A61B 5/0482
See application file for complete search history.

(56) References Cited

U.S. PATENT DOCUMENTS

| 7,166,070 | B2 * | 1/2007 | Lawlis | ............. | A61M 21/00 600/28 |
| 2004/0233060 | A1 | 11/2004 | Mohri | | |
| 2008/0243197 | A1 * | 10/2008 | Bove | .................. | A61N 1/40 607/2 |
| 2008/0319252 | A1 * | 12/2008 | Chapman | ............ | A61M 21/02 600/27 |

(Continued)

FOREIGN PATENT DOCUMENTS

| JP | 04-295372 | 10/1992 |
| JP | 2003-299637 | 10/2003 |
| JP | 2004-146630 | 5/2004 |

OTHER PUBLICATIONS

International Search Report; International Application No. PCT/JP2013/062623; Filed: Apr. 30, 2013. (Form PCT/ISA/210).

*Primary Examiner* — John Lacyk
(74) *Attorney, Agent, or Firm* — Chip Law Group

(57) ABSTRACT

There is provided a content output device including a selection unit which selects content according to a user's condition and a magnetic field pattern corresponding to the content, a content output unit which outputs the content, and a magnetic field generating unit which generates a magnetic field based on the magnetic field pattern.

8 Claims, 7 Drawing Sheets

(56) References Cited

U.S. PATENT DOCUMENTS

| | | | |
|---|---|---|---|
| 2010/0048985 A1* | 2/2010 | Henke | A61B 5/02055 600/28 |
| 2010/0179371 A1* | 7/2010 | Pletnev | A61N 2/002 600/9 |
| 2011/0015469 A1* | 1/2011 | Walter | A61M 21/02 600/27 |
| 2014/0148657 A1* | 5/2014 | Hendler | A61B 5/0476 600/301 |

* cited by examiner

FIG.4

| TIME SLOT | CHARACTERISTICS OF CONTENT | MAGNETIC STIMULATION SITE |
|---|---|---|
| MORNING | FRESH/BRIGHT | MOTOR AREA |
| NOON | ACTIVE/SPEEDY/ENERGETIC | CEREBRAL LIMBIC SYSTEM |
| NIGHT | RELAX/GRACEFUL | LATERAL PREFRONTAL AREA |

SETTING INFORMATION

FIG.5

| OPERATION INFORMATION | CHARACTERISTICS OF CONTENT | MAGNETIC STIMULATION SITE |
|---|---|---|
| WANT TO FEEL HAPPY | FRESH/BRIGHT | MOTOR AREA |
| WANT TO CONCENTRATE | ACTIVE/SPEEDY/ENERGETIC | CEREBRAL LIMBIC SYSTEM |
| WANT TO FEEL CALM | RELAX/GRACEFUL | LATERAL PREFRONTAL AREA |

SETTING INFORMATION

FIG.6

| BIOLOGICAL CONDITION | CHARACTERISTICS OF CONTENT | MAGNETIC STIMULATION SITE |
|---|---|---|
| UNPLEASANT | FRESH/BRIGHT | MOTOR AREA |
| EXCITEMENT | ACTIVE/SPEEDY/ENERGETIC | CEREBRAL LIMBIC SYSTEM |
| ANXIETY | RELAX/GRACEFUL | LATERAL PREFRONTAL AREA |

SETTING INFORMATION

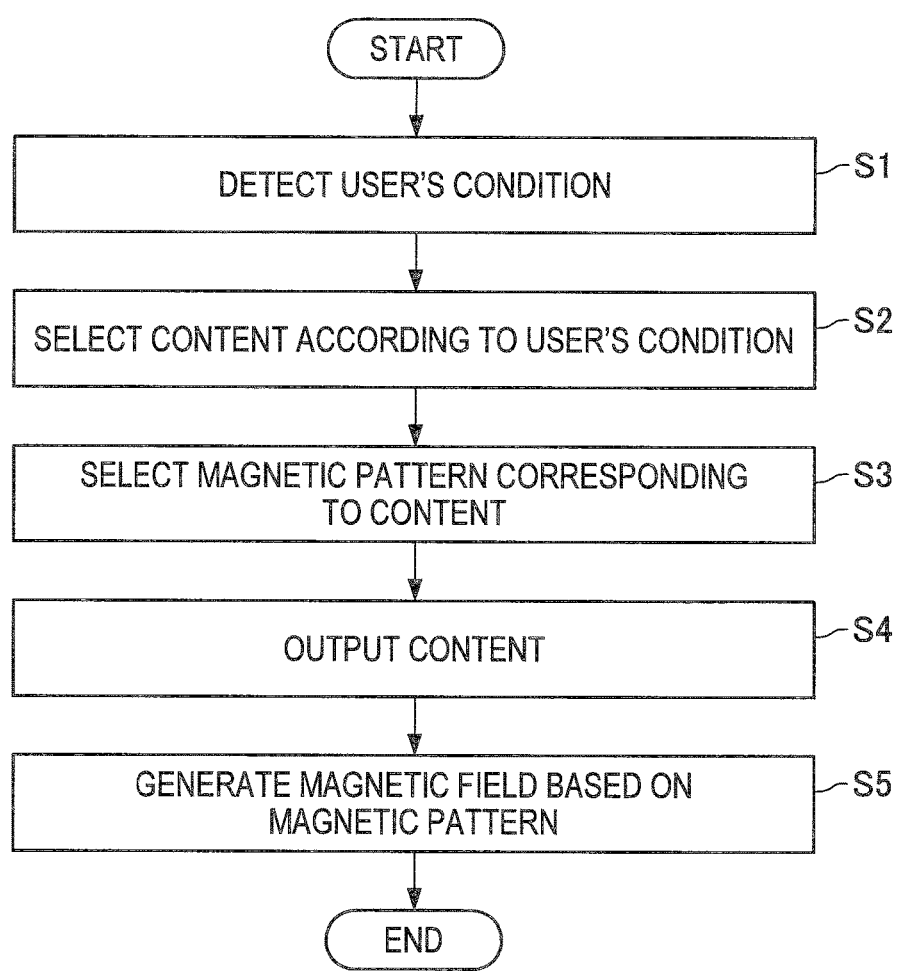

CONTENT OUTPUT DEVICE, CONTENT OUTPUT METHOD, CONTROL DEVICE, AND CONTROL METHOD

TECHNICAL FIELD

The present disclosure relates to a content output device, a content output method, a control device, and a control method.

BACKGROUND ART

In recent years, the spread of mobile terminals, such as audio players and smart phones, has allowed users to easily reproduce various kinds of content, such as music and moving images, and enjoy the same with the mobile terminals. On the other hand, kinds of content which can be provided to users also increase with an increase in content providers, so that work in which users search desired content among large amounts of content has also become complicated.

Then, for example, a technique of selecting content based on detected user's biological information is disclosed (for example, Patent Literature 1). According to the technique, content based on a user's condition is selected while saving user's time and effort for searching desired content from large amounts of content, and then the selected content can be provided to the user.

CITATION LIST

Patent Literature

SUMMARY OF INVENTION

Technical Problem

However, with this technique, even when the content according to the user's condition is selected, user's mental health maintenance cannot be sufficiently promoted only by providing the content according to the user's condition to the user. Therefore, it is desirable to realize a technique for sufficiently promoting the user's mental health maintenance.

Solution to Problem

According to the present disclosure, there is provided a content output device including a selection unit which selects content according to a user's condition and a magnetic field pattern corresponding to the content, a content output unit which outputs the content, and a magnetic field generating unit which generates a magnetic field based on the magnetic field pattern.

According to the present disclosure, there is provided a content output method including selecting content according to a user's condition and a magnetic field pattern corresponding to the content, outputting the content, and generating a magnetic field based on the magnetic field pattern.

According to the present disclosure, there is provided a control device including a selection unit which selects content according to a user's condition and a magnetic field pattern corresponding to the content, a content control unit which performs control in a manner that the content is output, and a magnetic field control unit which performs control in a manner that a magnetic field is generated based on the magnetic field pattern.

According to the present disclosure, there is provided a control method including selecting content according to a user's condition and a magnetic field pattern corresponding to the content, performing control in a manner that the content is output, and performing control in a manner that a magnetic field is generated based on the magnetic field pattern.

Advantageous Effects of Invention

As described above, the present disclosure can provide a technique for sufficiently promoting the user's mental health maintenance.

BRIEF DESCRIPTION OF DRAWINGS

FIG. 4 is a view illustrating an example of the configuration of setting information to be used by a content output device according to an embodiment of the present disclosure.

FIG. 5 is a view illustrating an example of the configuration of setting information to be used by a content output device according to an embodiment of the present disclosure.

FIG. 6 is a view illustrating an example of the configuration of setting information to be used by a content output device according to an embodiment of the present disclosure.

FIG. 7 is a view illustrating an example of an operation of a content output device according to an embodiment of the present disclosure.

DESCRIPTION OF EMBODIMENTS

Figure 1:
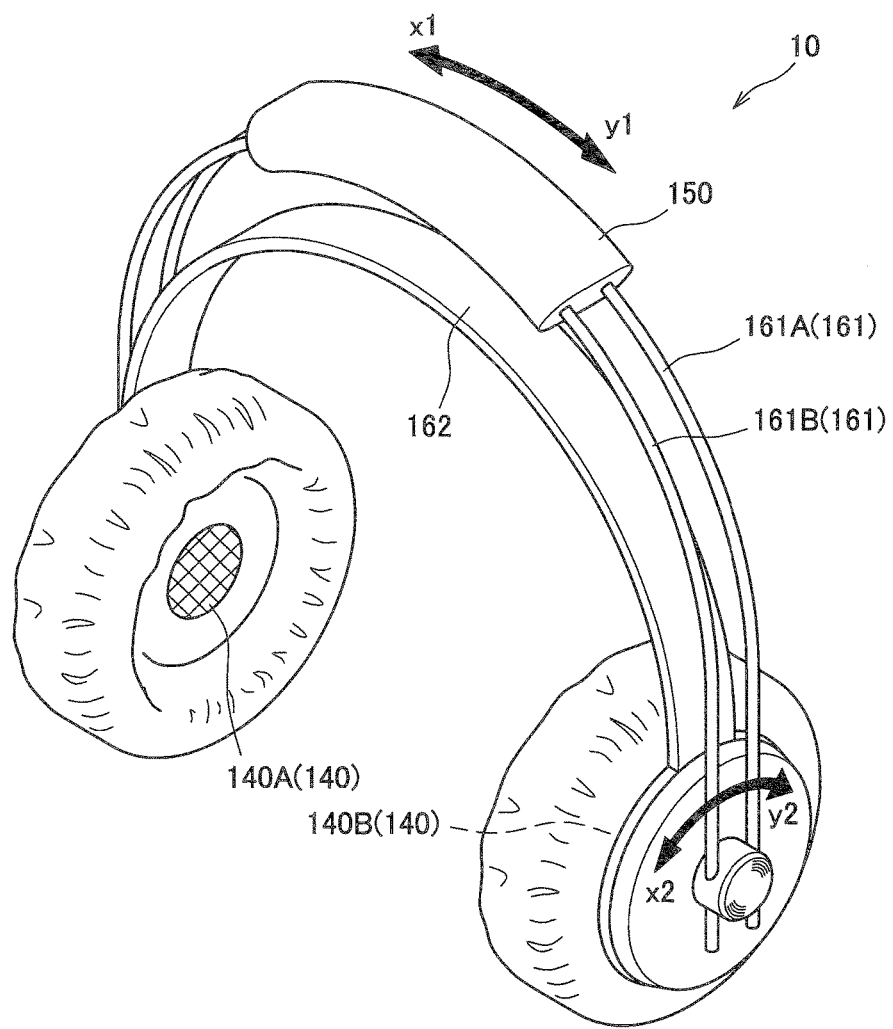
FIG. 1 is a view illustrating an example of the appearance of a content output device according to an embodiment of the present disclosure.

Hereinafter, preferred embodiments of the present invention will be described in detail with reference to the appended drawings. Note that, in this specification and the drawings, elements that have substantially the same function and structure are denoted with the same reference signs, and repeated explanation is omitted.

In the present specification and drawings, a plurality of constituent elements having substantially the same functional configuration may be distinguished by different alphabets attached after the same reference numerals. However, when each of a plurality of elements having substantially the same functional configuration need not be especially distinguished, only the same reference sign is assigned thereto.

"Description of Embodiments" is described according to the item order described below.

1. Example of Appearance of Content Output Device
2. Example of Functional Configuration of Content Output Device
3. Example of Operation of Content Output Device
4. Conclusion

1. Example of Appearance of Content Output Device

First, an example of the appearance of a content output device 10 according to an embodiment of the present disclosure is described. FIG. 1 is a view illustrating an example of the appearance of the content output device 10 according to the embodiment of the present disclosure. As illustrated in FIG. 1, in this specification, it is assumed that the content output devices 10 is a headband type headphone and content includes sound data but the type of the headphone is not limited to such an example. For example, the type of the headphone may be a type other than the headband type (for example, a neck band type, an ear hook type, and the like).

When the content output device 10 is a headband type headphone, the content output device 10 has content output units 140A and 140B, a magnetic field generating unit 150, fixing units 161A and 161B, and a band portion 162 as illustrated in FIG. 1. A user wears the content output device 10 on the user's head in such a manner as to fix the band portion 162 to the user's head, and then performs a content reproduction operation. Then, the user can hear sound obtained by reproducing content from the content output units 140A and 140B.

By outputting content to the user, the user's mental health maintenance can be promoted. However, the user's mental health maintenance is not necessarily sufficiently promoted only by the output of content.

On the other hand, as disclosed in Literature A, for example, (Proved in terms of brain science that "Energy and Motivation" are associated with the motor function recovery by rehabilitation, http://www.jst.go.jp/pr/announce/20110929/index.html), a finding has been obtained that the motor function recovery can be effectively advanced by activating the work of the cerebral limbic system which is the neural circuit of the brain which controls emotions.

Moreover, as disclosed in Literature B, for example, (NHK Special, "Latest depression treatment light topography inspection transcranial magnetic stimulation TMS deep brain stimulation DBS cognitive behavioral therapy DLPFC amygdala 25-area bipolar disorder schizophrenia, Serika Hospital "More information: http://topicsnow.blog72.fc2.com/blog-entry-4103.html), a finding has been obtained that magnetic stimulation to the brain is effective for medical treatment of depression.

Moreover, as disclosed in Literature C, for example, (Research on the action mechanism of repetitive transcranial magnetic stimulation (rTMS) and deep brain stimulation (DBS), http://kaken.nii.ac.jp/d/p/14580764), a finding has been obtained that an increase in dopamine metabolism by the repetitive transcranial magnetic stimulation (rTMS) to the motor area is effective medical treatment of depression and the like.

Thus, this embodiment proposes to output content to a user and also performs magnetic stimulation to the user's brain to thereby sufficiently promote the user's mental health maintenance.

Specifically, the magnetic field generating unit 150 of the content output device 10 is fixed by the fixing units 161A and 161B, for example, has a coil inside, and can pass a current to the coil to thereby generate a magnetic field therearound. The magnetic field generated by the magnetic field generating unit 150 can be made to act on the user's head. More specifically, magnetic stimulation may be given to the user's brain. Electric power may be able to be supplied to the magnetic field generating unit 150 through the fixing units 161A and 161B.

For example, as illustrated in FIG. 1, the magnetic field generating unit 150 is designed to be movable on the fixing units 161A and 161B (for example, movable in x1 direction or y1 direction illustrated in FIG. 1) and may be adjusted in the horizontal direction of the user's head. Moreover, as illustrated in FIG. 1, the magnetic field generating unit 150 is designed to be rotatable with the fixing units 161A and 161B (for example, rotatable in x2 direction or y2 direction illustrated in FIG. 1) and may be adjusted in the front-rear direction of the user's head.

Thus, the strength of the magnetic stimulation to a specific portion (for example, motor area, cerebral limbic system, lateral prefrontal area, and the like) in the user's brain can be changed by the adjustment of the position of the magnetic field generating unit 150 or the strength of the magnetic stimulation to either the right brain or the left brain can be changed. The position of the magnetic field generating unit 150 may be adjusted by a user's manual operation or may be automatically changed by the content output device 10. The strength of the magnetic stimulation is not particularly limited and may be high frequency magnetic stimulation of 5 Hz or higher, for example, as disclosed in Literature E.

The magnetic field generation by the magnetic field generating unit 150 may be performed by any technique. For example, the magnetic field generation may be performed by the transcranial magnetic stimulation (TMS) as disclosed in Literature D (JP 2009-22660A), for example. As described in Literature D, TMS is the technique in which a current is passed to a coil (for example, 8-shaped coil) placed on the scalp to generate a magnetic field, and then an induced current thereof is generated in the brain, whereby the nerve function of a magnetic stimulation site is temporarily excited or suppressed.

Alternatively, the magnetic field generation by the magnetic field generating unit 150 may be performed by various kinds of stimulation methods disclosed in Literature E, for example, (Miyuki Giken Web seminar Vol. 4, Magnetic stimulation technical note for research, http://www.miyuki-net.co.jp/jp/seminar/msTechnicalNote/msTechnicalNote.shtml).

The content output device 10 may be one other than the headphone. For example, the content output device 10 may be a HMD (Head Mounted Display) and the content may be image data. In this case, when a user wears the content output device 10 on the head and performs a content reproduction operation, the user can browse an image obtained by reproducing the content from the content output units 140A and 140B.

Thus, the description above describes the example of the appearance of the content output device 10 according to the embodiment of the present disclosure.

2. Example of Functional Configuration of Content Output Device

Figure 2:
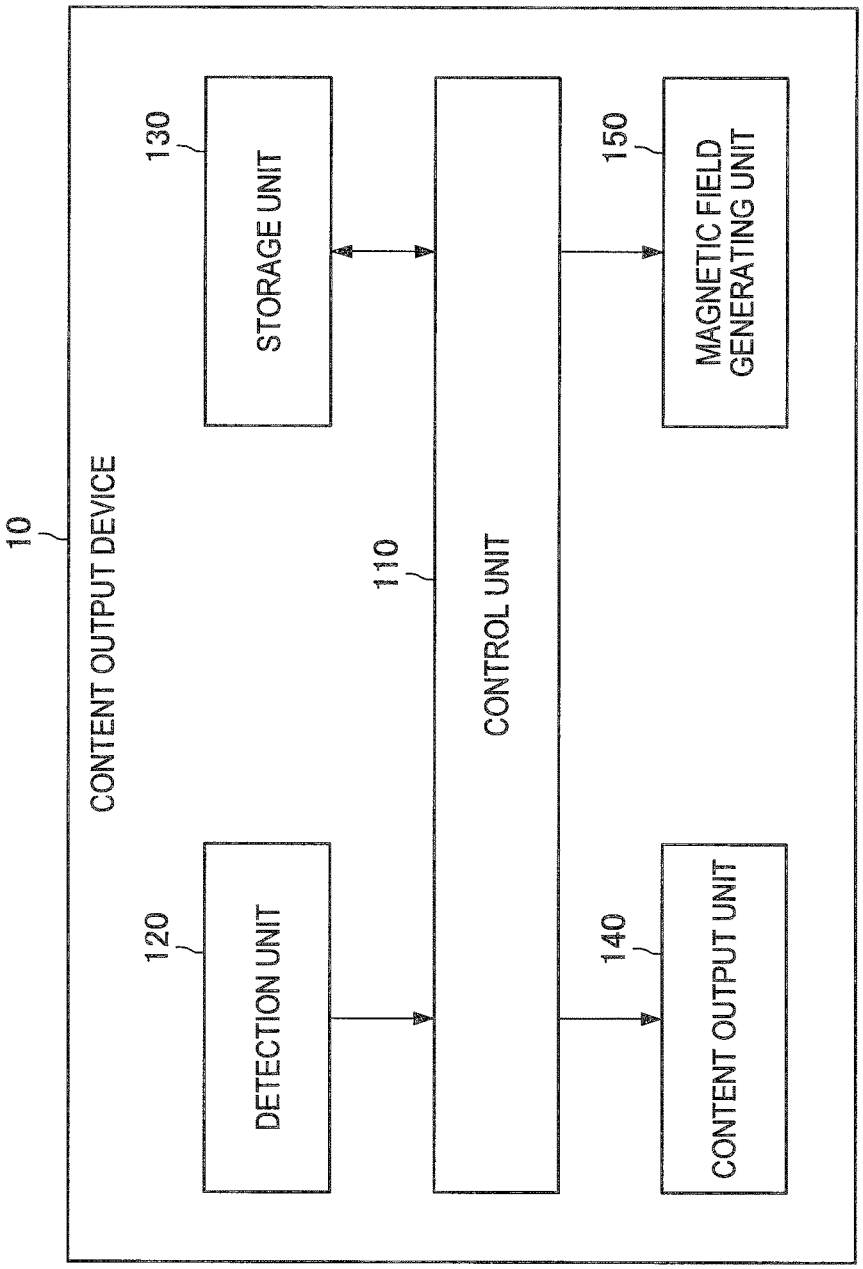
FIG. 2 is a view illustrating an example of the functional configuration of a content output device according to an embodiment of the present disclosure.

Then, an example of the functional configuration of the content output device 10 according to the embodiment of the present disclosure is described. FIG. 2 is a view illustrating an example of the functional configuration of the content output device 10 according to the embodiment of the present disclosure. As illustrated in FIG. 2, the content output device 10 has a control unit 110, a detection unit 120, a storage unit 130, a content output device 140, and a magnetic field generating unit 150.

The control unit 110 is equivalent to a processor, such as Central Processing Unit (CPU), for example. The control unit 110 exhibits various functions of the control unit 110 by executing programs stored in the storage unit 130 or other storage media. The control unit 110 can function as a control device.

The detection unit 120 has a function of detecting a user's condition. Moreover, the detection unit 120 outputs a detected user's condition to the control unit 110. The user's condition is used for selection of content, for example, by the control unit 110. The detection unit 120 is united with the content output device 10 in the example illustrated in FIG. 2 but the detection unit 120 may be separately constituted from the content output device 10. The details of the function of the detection unit 120 are described later.

The storage unit 130 stores a program for operating the control unit 110 using a storage medium, such as a semiconductor memory or a hard disk. Moreover, for example, the storage unit 130 can also store various kinds of data (for example, setting information, content, and the like) to be used by the program. The details of the data are described later. The storage unit 130 is united with the content output device 10 in the example illustrated in FIG. 2 but the storage unit 130 may be separately constituted from the content output device 10.

The content output device 140 has a function of outputting content. For example, the content output device 140 outputs content according to the control by the control unit 110. As described above, when the content output device 10 is a headphone and the content includes sound data, for example, the content output device 140 may be a sound output device which outputs sound obtained by reproducing the content. When the content output device 10 is a HMD and the content includes image data for example, the content output device 140 may be a display of outputting an image obtained by reproducing the content.

The magnetic field generating unit 150 has a function of generating a magnetic field. For example, the magnetic field generating unit 150 generates a magnetic field according to the control by the control unit 110. As described above, the magnetic field generating unit 150 has a coil inside, for example, and can pass a current to the coil to thereby generate a magnetic field therearound. The magnetic field generated by the magnetic field generating unit 150 can be made to act on the user's head. The strength, frequency, and position of the magnetic field generated by the magnetic field generating unit 150, the period in which the magnetic field is generated, and the like may be controlled by the control unit 110.

As described above, in this embodiment, content is output to a user and also magnetic stimulation is performed to the user's brain, whereby the user's mental health maintenance is sufficiently promoted. The description below mainly describes combination variations of the output of content to a user and the magnetic stimulation to the user's brain and proposes a technique of more effectively promoting the user's mental health maintenance.

Figure 3:
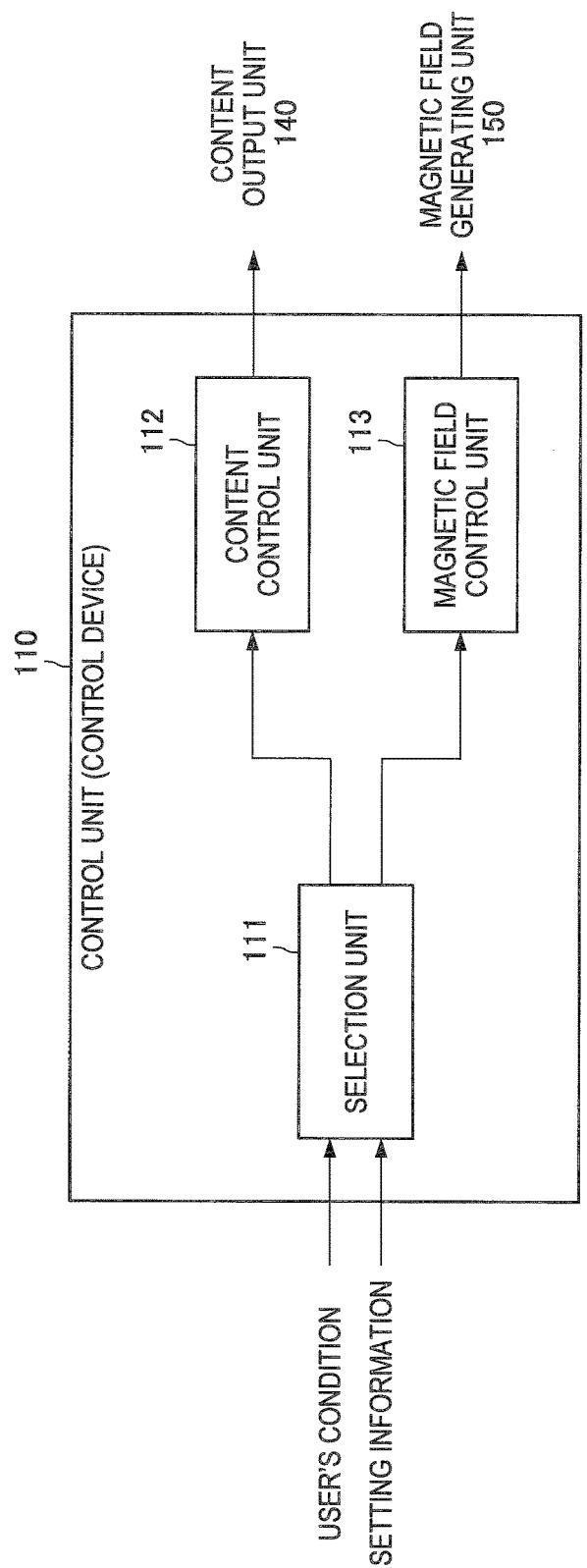
FIG. 3 is a view illustrating an example of the functional configuration of a control unit according to an embodiment of the present disclosure.

FIG. 3 is a view illustrating an example of the functional configuration of the control unit 110 according to the embodiment of the present disclosure. As illustrated in FIG. 3, the control unit 110 has a selection unit 111, a content control unit 112, and a magnetic field control unit 113. The details of the function of each of the selection unit 111, the content control unit 112, and the magnetic field control unit 113 are described later.

FIG. 4 is a view illustrating an example of the configuration of setting information to be used by the content output device 10 according to the embodiment of the present disclosure. In the example illustrated in FIG. 4, the setting information is constituted in such a manner that the time slot where a user is present and the characteristics of content are matched and the characteristics of content and magnetic stimulation sites are matched. However, the time slot in which a user is present is an example of a user's condition and the magnetic stimulation site is equivalent to the position of a magnetic field and is merely an example of a magnetic field pattern.

More specifically, the setting information is information in which a user's condition, the characteristics of content, and a magnetic field pattern are matched. As the magnetic field pattern, the strength of the magnetic field may be used, the frequency of the magnetic field may be used, or a period in which the magnetic field is generated may be used, in place of the magnetic stimulation site. The setting information is stored by the storage unit 130 beforehand and may be acquired by the control unit 110 as required, for example. The setting information stored by the storage unit 130 may be updated as appropriate.

In the setting information illustrated in FIG. 4, the time slot in which a user is present is indicated as "Morning", "Daytime", and "Night" but a manner of dividing each time slot is not particularly limited. For example, each time slot may be divided by time. The characteristics of content are indicated as "Fresh/Bright", "Active/Speedy/Energetic", and "Relax/Graceful" but the kinds of the characteristics of content are not limited to the example illustrated in FIG. 4. The characteristics of content are acquired as analysis results of the quantity of the characteristics of content, for example.

Moreover, in FIG. 4, the magnetic stimulation site is indicated as "Motor area", "Cerebral limbic system", and "Lateral prefrontal area" but the kinds of the magnetic stimulation sites are not limited to the example illustrated in FIG. 4. For example, it is known to be useful for depression medical treatment or suppressing feeling, such as anxiety, fear, and sadness, to give magnetic stimulation to the "Lateral prefrontal area" as disclosed in Literature E. Therefore, it is assumed to be useful that the magnetic stimulation site "Lateral prefrontal area" is matched to the characteristics of content "Relax/Graceful." Thus, it is predicted that the user's mental health maintenance can be more effectively promoted.

Thus, in this embodiment, the user's condition, the characteristics of content, and the magnetic field pattern are matched. The content having the characteristics corresponding to the user's condition is provided to a user and also a magnetic field is generated based on a magnetic field pattern corresponding to the characteristics of the content to cause the magnetic field to act on the user's head, whereby the user's mental health maintenance can be more effectively promoted. The matching of the characteristics of content and the magnetic field pattern can be added or changed as appropriate based on a finding when this embodiment is applied.

Specifically, first, the selection unit 111 selects content according to a user's condition and a magnetic field pattern corresponding to the content. For example, the selection unit 111 selects the characteristics of the content corresponding to the user's condition and the magnetic field pattern corresponding to the characteristics of the content. Then, the content control unit 112 controls the content output device 140 in such a manner that the content selected by the selection unit 111 is output from the content output device 140.

Although the content output from the content output device 140 is reproduced content, the reproduction of the content may be performed by the content control unit 112 or may be performed in a device outside the content output device 10. The content output device 140 outputs content according to the control by the content control unit 112.

On the other hand, the magnetic field control unit 113 controls the magnetic field generating unit 150 in such a manner that a magnetic field based on a magnetic field pattern selected by the selection unit 111 is generated by the magnetic field generating unit 150. The magnetic field generating unit 150 generates a magnetic field according to the control by the magnetic field control unit 113. As described above, the magnetic field pattern is equivalent to the strength, frequency, and position of the magnetic field, a period in which the magnetic field is generated, and the like. The magnetic field generating unit 150 can cause the generated magnetic field to act on the user's head.

The user's condition may be detected by the detection unit 120, for example. Although the user's condition is not particularly limited but may be a time slot in which a user is present, for example. More specifically, the detection unit 120 may detect the time slot in which a user is present as the user's condition. For example, the detection unit 120 may detect the time slot to which the present time belongs as the time slot in which a user is present.

For example, in the example illustrated in FIG. 4, when the time slot "night" in which a user is present is detected by the detection unit 120, the selection unit 111 may select the content having the characteristics "Relax/Graceful" of the content corresponding to the time slot "night". The selection unit 111 may select the magnetic stimulation site "Lateral prefrontal area" corresponding to the characteristics Relax/Graceful" of the content.

FIG. 5 is a view illustrating an example of the configuration of the setting information to be used by the content output device 10 according to the embodiment of the present disclosure. In the example illustrated in FIG. 5, the setting information is constituted in such a manner that operation information from a user and the characteristics of content are matched and the characteristics of content and magnetic stimulation sites are matched. However, the operation information is an example of a user's condition and the magnetic stimulation site is equivalent to the position of a magnetic field and is merely an example of a magnetic field pattern. The characteristics of content and the magnetic stimulation sites are as described above.

In the setting information illustrated in FIG. 5, the operation information is indicated as "Want to feel happy", "Want to concentrate", and "Want to feel calm" but the kind of the operation information is not particularly limited. For example, when the operation information is used as the user's condition, the detection unit 120 may detect the operation information as the user's condition. For example, it is constituted so that a user can input, into the detection unit 120, the information showing any one of the operations of "Want to feel happy", "Want to concentrate", "Want to feel calm", and the like as the operation information.

For example, in the example illustrated in FIG. 5, when the operation information "Want to feel calm" is detected by the detection unit 120, the selection unit 111 may select the content having the characteristics "Relax/Graceful" of the content corresponding to the operation information "Want to feel calm." The selection unit 111 may select the magnetic stimulation site "Lateral prefrontal area" corresponding to the characteristics of the content "Relax/Graceful".

FIG. 6 is a view illustrating an example of the configuration of the setting information to be used by the content output device 10 according to the embodiment of the present disclosure. In the example illustrated in FIG. 6, the setting information is constituted in such a manner that a user's biological condition and the characteristics of content are matched and the characteristics of content and the magnetic stimulation sites are matched. However, the biological condition is an example of the user's condition and the magnetic stimulation site is equivalent to the position of a magnetic field and is merely an example of a magnetic field pattern. The characteristics of content and the magnetic stimulation sites are as described above.

In the setting information illustrated in FIG. 6, although the biological conditions are illustrated as "Unpleasant", "Excitement", and "Anxiety", the kinds of the biological conditions are not particularly limited. For example, when the biological condition is used as the user's condition, the detection unit 120 may detect the biological condition as the user's condition. The biological condition may be user's brain waves, may be a user's pulse rate per unit time, may be a user's body temperature, may be a user's blood pressure, may be a user's sweat volume, or may be another condition, for example.

As the detection technique of the user's brain waves, various techniques are can be employed. For example, in recent years, a noninvasive brain function measuring method referred to as a functional near-infrared spectroscopy (fNIRS) has been established as disclosed in Literature D. The fNIRS is a technique of optically measuring an increase or decrease of oxyhemoglobin or deoxyhemoglobin of the organization from the body surface (head surface) by near-infrared light and is a technique capable of measuring the same even in a state where a target person is exercising. Therefore, for example, the fNIRS can be employed as the detection technique of the user's brain waves.

For example, in the example illustrated in FIG. 6, when the biological condition "Anxiety" is detected by the detection unit 120, the selection unit 111 may select the content having the characteristics "Relax/Graceful" of the content corresponding to the biological condition "Anxiety". Moreover, the selection unit 111 may select the magnetic stimulation site "Lateral prefrontal area" corresponding to the characteristics "Relax/Graceful" of the content.

The description above describes the example of the functional configuration of the content output device 10 according to the embodiment of the present disclosure described.

3. Example of Operation of Content Output Device

Then, an example of an operation of the content output device 10 according to the embodiment of the present disclosure is described. FIG. 7 is a view illustrating an example of an operation of the content output device 10 according to the embodiment of the present disclosure. As illustrated in FIG. 7, first, the detection unit 120 detects a user's condition (S1). Then, the selection unit 111 selects content according to the user's condition (S2), and then selects a magnetic field pattern corresponding to the content (S3).

Then, the content control unit 112 controls the content output device 140 so that the content selected by the selection unit 111 is output by the content output device 140, and then the content output device 140 outputs the content according to the control by the content control unit 112 (S4). The magnetic field control unit 113 controls the magnetic field generating unit 150 so that a magnetic field is generated by the magnetic field generating unit 150 based on a magnetic field pattern selected by the selection unit 111, and then the magnetic field generating unit 150 generates a magnetic field according to the control by the magnetic field control unit 113 (S5).

According to the operation example, content according to the user's condition is output to a user and also magnetic stimulation corresponding to the content is given to the user's brain, whereby the user's mental health maintenance can be sufficiently promoted.

4. Conclusion

As described above, the embodiment of the present disclosure can provide the content output device 10 having the selection unit 111 which selects content according to a user's condition and a magnetic field pattern corresponding to the content, the content output device 140 which outputs content, and the magnetic field generating unit 150 which generates a magnetic field based on a magnetic field pattern. According to this configuration, content according to the user's condition is output to a user and also magnetic stimulation corresponding to the content is given to the user's brain, whereby the user's mental health maintenance can be sufficiently promoted.

Moreover, the embodiment of the present disclosure can also provide the control device 110 having the selection unit 111 which selects content according to a user's condition and a magnetic field pattern corresponding to the content, the content control unit 112 which performs control so that content is output, and the magnetic field control unit 113 which performs control so that a magnetic field is generated based on a magnetic field pattern. According to this configuration, control is performed so that content according to the user's condition is output to a user and also control is performed so that magnetic stimulation corresponding to the content is given to the user's brain, whereby the user's mental health maintenance can be sufficiently promoted.

Moreover, according to the embodiment of the present disclosure, "Depression patients", the number of which is assumed to be 1 million in Japan at the present time, for example, can be saved and the labor force obtained by the generation in their most productive years can be recovered, so that they can be expected to greatly contribute to society. However, it is a matter of course that the content output device 10 according to the embodiment of the present disclosure may be used also for users other than the "Depression patients".

The content output device 10 according to the embodiment of the present disclosure is a device which can be used by all users irrespective of whether or not the user is a "Depression patient" and can sufficiently promote the user's mental health maintenance. Thus, it is expected that all users' positive feeling is supported.

Furthermore, it is expected that the content output device 10 according to the embodiment of the present disclosure is used by a large number of users and achieves health maintenance of the mental health of a large number of users, so that society is revitalized and moves into an era in which a large number of users can realize not only "material abundance" but "mental abundance".

The preferred embodiments of the present invention have been described above with reference to the accompanying drawings, whilst the present invention is not limited to the above examples, of course. A person skilled in the art may find various alternations and modifications within the scope of the appended claims, and it should be understood that they will naturally come under the technical scope of the present invention.

For example, each step in the operation example of the content output device 10 of this specification is not necessarily performed in time series in accordance with the order described as the flow chart. For example, each step in the operation example of the content output device 10 may be processed in an order different from the order described as the flow chart or may be processed in a parallel manner.

Moreover, a program for causing hardware built in a computer, such as CPU, ROM, and RAM, to demonstrate functions equivalent to the configuration of the control device 110 described above can also be created. Moreover, a recording medium which records the program and which can be read by a computer may also be provided.

Additionally, the present technology may also be configured as below.

(1)

A content output device including:

a selection unit which selects content according to a user's condition and a magnetic field pattern corresponding to the content;

a content output unit which outputs the content; and a magnetic field generating unit which generates a magnetic field based on the magnetic field pattern.

(2)

The content output device according to (1), further including:

a detection unit which detects the user's condition, wherein the selection unit selects content according to the user's condition detected by the detection unit and a magnetic field pattern corresponding to the content.

(3)

The content output device according to (2), wherein the detection unit detects a biological condition of the user as the user's condition.

(4)

The content output device according to (2), wherein the detection unit detects a time slot in which the user is present as the user's condition.

(5)

The content output device according to (2), wherein the detection unit detects operation information from the user as the user's condition.

(6)

The content output device according to any one of (1) to (5), wherein the content output device is mounted on a head of the user, and the magnetic field generating unit causes the magnetic field to act on the head of the user.

(7)

A content output method including:

selecting content according to a user's condition and a magnetic field pattern corresponding to the content;

outputting the content; and generating a magnetic field based on the magnetic field pattern.

(8)

A control device including:

a selection unit which selects content according to a user's condition and a magnetic field pattern corresponding to the content;

a content control unit which performs control in a manner that the content is output; and a magnetic field control unit which performs control in a manner that a magnetic field is generated based on the magnetic field pattern.

(9)

A control method including:

selecting content according to a user's condition and a magnetic field pattern corresponding to the content;

performing control in a manner that the content is output; and performing control in a manner that a magnetic field is generated based on the magnetic field pattern.

REFERENCE SIGNS LIST 10 content output unit
110 control unit
111 selection unit
112 content control unit
113 magnetic field control unit
120 detection unit
130 storage unit
140 (140A, 140B) content output unit
150 magnetic field generating unit
161 (161A, 161B) holding unit
162 band portion

The invention claimed is:

1. A content output device, comprising:
a central processing unit (CPU) configured to:
   detect a user condition that indicates a user emotional state;
   select content based on the user condition;
   select a magnetic field pattern based on the content;
   control output of the content via one of a speaker or a display device; and
   control a magnetic field generator to generate a magnetic field based on the magnetic field pattern.

2. The content output device according to claim 1, wherein the CPU is further configured to detect a user biological condition as the user condition.

3. The content output device according to claim 1, wherein the CPU is further configured to detect a time slot that indicates a time of day as the user condition.

4. The content output device according to claim 1, wherein the content output device is one of a headphone or a Head Mounted Display (HMD) device.

5. A content output method, comprising:
in a content output device:
   detecting a user condition that indicates a user emotional state;
   selecting content based on the user condition;
   selecting a magnetic field pattern based on the content;
   outputting the content via one of a speaker or a display device; and
   generating a magnetic field based on the magnetic field pattern.

6. A control device, comprising:
a central processing unit (CPU) configured to:
   detect a user condition that indicates a user emotional state;
   select content based on the user condition;
   select a magnetic field pattern based on the content;
control output of the content via one of a speaker or a display device; and
control generation of a magnetic field based on the magnetic field pattern.

7. A control method, comprising:
in a control device:
   detecting a user condition that indicates a user emotional state;
   selecting content based on the user condition;
   selecting a magnetic field pattern based on the content;
   controlling output of the content via one of a speaker or a display device; and
   controlling generation of a magnetic field, based on the magnetic field pattern.

8. The content output device according to claim 1, wherein the CPU is further configured to:
receive operation information based on user input; and
detect the operation information as the user condition.

* * * * *